(12) United States Patent
Kerr et al.

(10) Patent No.: US 7,109,986 B2
(45) Date of Patent: Sep. 19, 2006

(54) ILLUMINATION APPARATUS

(75) Inventors: Roger S. Kerr, Brockport, NY (US);
Timothy J. Tredwell, Fairport, NY (US); Eric J. Donaldson, St. Paul, MN (US); Badhri Narayan, Rochester, NY (US); Sarat K. Mohapatra, Woodbury, MN (US)

(73) Assignee: Eastman Kodak Company, Rochester, NY (US)

( * ) Notice: Subject to any disclaimer, the term of this patent is extended or adjusted under 35 U.S.C. 154(b) by 249 days.

(21) Appl. No.: 10/717,347

(22) Filed: Nov. 19, 2003

(65) Prior Publication Data

US 2005/0184985 A1    Aug. 25, 2005

(51) Int. Cl.
G06F 17/00 (2006.01)
G06F 19/00 (2006.01)
G06F 17/21 (2006.01)
G06F 17/24 (2006.01)
G06Q 99/00 (2006.01)
H04K 1/00 (2006.01)
H04L 9/00 (2006.01)

(52) U.S. Cl. .................. 345/418; 705/3; 705/54; 705/57; 705/58; 705/59; 715/512

(58) Field of Classification Search ............... 345/418; 715/512; 705/3, 54, 57, 58, 59
See application file for complete search history.

(56) References Cited

U.S. PATENT DOCUMENTS

| 3,580,565 A | 5/1971 | Mallory et al. |
| 3,713,148 A | 1/1973 | Cardullo et al. |
| 3,750,167 A * | 7/1973 | Gehman et al. ............. 342/44 |
| 3,835,301 A | 9/1974 | Barney |
| 4,075,018 A | 2/1978 | Custer |
| 4,129,855 A | 12/1978 | Rodrian |
| 4,178,183 A | 12/1979 | Ciurca, Jr. et al. |
| 4,208,210 A | 6/1980 | Sakai et al. |
| 4,247,758 A | 1/1981 | Rodrian |
| 4,270,853 A | 6/1981 | Hatada et al. |
| 4,270,854 A | 6/1981 | Stemme et al. |
| 4,275,103 A | 6/1981 | Tsubusaki et al. |
| 4,394,441 A | 7/1983 | Kawaguchi et al. |

(Continued)

FOREIGN PATENT DOCUMENTS

JP    02-164872    6/1990

(Continued)

OTHER PUBLICATIONS

TEMIC Semiconductors, E5550-TK5550—Read/Write Transponder, pp. 1-7, www.eurochip.com/tech_server/tag/E5550%20Datasheet.pdf.

(Continued)

*Primary Examiner*—Ulka Chauhan
*Assistant Examiner*—Roberta Prendergast
(74) *Attorney, Agent, or Firm*—Roland R. Schindler, II

(57) ABSTRACT

A viewing device is provided for viewing at least one image transparency having an associated tracking memory. The viewing device comprises an illumination device having at least one viewing surface adapted to present at least one illumination pattern, at least one radio frequency read write device for obtaining electronic data stored in an associated tracking memory of an image transparency positioned proximate to the viewing surface and at least one display device for viewing at least one electronic image related to said at least one image transparency. A control processing unit is adapted to receive said obtained data from said associated tracking memory and to use the obtained data for forming the at least one electronic image.

29 Claims, 2 Drawing Sheets

U.S. PATENT DOCUMENTS

| | | | |
|---|---|---|---|
| 4,416,963 A | 11/1983 | Takimoto et al. | |
| 4,418,141 A | 11/1983 | Kawaguchi et al. | |
| 4,431,764 A | 2/1984 | Yoshizumi | |
| 4,495,276 A | 1/1985 | Takimoto et al. | |
| 4,571,361 A | 2/1986 | Kawaguchi et al. | |
| 4,600,280 A | 7/1986 | Clark | |
| 4,663,625 A | 5/1987 | Yewen | |
| 4,742,470 A | 5/1988 | Juengel | |
| 4,806,958 A | 2/1989 | Momot et al. | |
| 4,855,769 A | 8/1989 | Slavitter et al. | |
| 4,880,325 A | 11/1989 | Ueda et al. | |
| 4,896,027 A * | 1/1990 | Drexler | 235/488 |
| 4,905,029 A | 2/1990 | Kelley | |
| 4,964,066 A * | 10/1990 | Yamane et al. | 345/441 |
| 4,983,996 A | 1/1991 | Kinoshita | |
| 4,990,092 A | 2/1991 | Cummings | |
| 4,999,276 A | 3/1991 | Kuwabaa et al. | |
| 5,008,661 A | 4/1991 | Raj | |
| 5,019,815 A | 5/1991 | Lemelson et al. | |
| 5,030,544 A | 7/1991 | Olbrechts et al. | |
| 5,049,898 A | 9/1991 | Arthur et al. | |
| 5,049,904 A | 9/1991 | Nakamura et al. | |
| 5,059,126 A | 10/1991 | Kimball | |
| 5,078,523 A | 1/1992 | McGourty et al. | |
| 5,104,247 A | 4/1992 | Ohshima | |
| 5,105,190 A | 4/1992 | Kip et al. | |
| 5,122,445 A | 6/1992 | Ishigaki | |
| 5,184,152 A | 2/1993 | French | |
| 5,185,315 A | 2/1993 | Sparer | |
| 5,196,846 A | 3/1993 | Brockelsby et al. | |
| 5,196,862 A | 3/1993 | Fisher, Sr. | |
| 5,224,784 A | 7/1993 | Haftmann et al. | |
| 5,266,968 A | 11/1993 | Stephenson | |
| 5,266,975 A | 11/1993 | Mochizuki et al. | |
| 5,268,708 A | 12/1993 | Harshbarger et al. | |
| 5,290,190 A | 3/1994 | McClanahan | |
| 5,293,313 A * | 3/1994 | Cecil et al. | 382/131 |
| 5,294,525 A | 3/1994 | Yamauchi et al. | |
| 5,297,881 A | 3/1994 | Ishiyama | |
| 5,300,575 A | 4/1994 | Jonas et al. | |
| 5,305,020 A | 4/1994 | Gibbons et al. | |
| 5,310,999 A | 5/1994 | Claus et al. | |
| 5,312,681 A | 5/1994 | Muys et al. | |
| 5,313,235 A | 5/1994 | Inoue et al. | |
| 5,318,370 A | 6/1994 | Nehowig | |
| 5,323,704 A | 6/1994 | Fraczek | |
| 5,331,338 A | 7/1994 | Mager | |
| 5,340,676 A | 8/1994 | Anderson et al. | |
| 5,342,671 A | 8/1994 | Stephenson | |
| 5,347,274 A | 9/1994 | Hassett | |
| 5,354,613 A | 10/1994 | Quintens et al. | |
| 5,365,312 A | 11/1994 | Hillmann et al. | |
| 5,368,995 A | 11/1994 | Christian et al. | |
| 5,370,981 A | 12/1994 | Krafft et al. | |
| 5,372,924 A | 12/1994 | Quintens et al. | |
| 5,382,494 A | 1/1995 | Kudo et al. | |
| 5,385,416 A | 1/1995 | Maekawa et al. | |
| 5,391,472 A | 2/1995 | Muys et al. | |
| 5,398,257 A | 3/1995 | Groenteman | |
| 5,403,467 A | 4/1995 | Jones et al. | |
| 5,426,011 A | 6/1995 | Stephenson | |
| 5,430,441 A | 7/1995 | Bickley et al. | |
| 5,440,678 A * | 8/1995 | Eisen et al. | 715/537 |
| 5,443,944 A | 8/1995 | Krafft et al. | |
| 5,455,617 A | 10/1995 | Stephenson et al. | |
| 5,459,021 A | 10/1995 | Ito et al. | |
| 5,466,576 A | 11/1995 | Schulz et al. | |
| 5,484,694 A | 1/1996 | Lelental et al. | |
| 5,491,327 A | 2/1996 | Saroya | |
| 5,491,468 A | 2/1996 | Everett et al. | |
| 5,493,385 A | 2/1996 | Ng | |
| 5,504,507 A | 4/1996 | Watrobski et al. | |
| 5,513,920 A | 5/1996 | Whritenor et al. | |
| 5,516,590 A | 5/1996 | Olmstead et al. | |
| 5,521,663 A | 5/1996 | Norris, III | |
| 5,528,222 A | 6/1996 | Moskowitz et al. | |
| 5,528,377 A | 6/1996 | Hutcheson | |
| 5,530,702 A * | 6/1996 | Palmer et al. | 370/445 |
| 5,532,727 A | 7/1996 | Agano et al. | |
| 5,537,920 A | 7/1996 | Hasegawa et al. | |
| 5,541,585 A * | 7/1996 | Duhame et al. | 340/5.62 |
| 5,547,501 A | 8/1996 | Maruyama et al. | |
| 5,559,578 A | 9/1996 | Umeda et al. | |
| 5,562,352 A | 10/1996 | Whritenor et al. | |
| 5,565,906 A | 10/1996 | Schoon | |
| 5,574,519 A | 11/1996 | Manico et al. | |
| 5,575,898 A | 11/1996 | Wolf et al. | |
| 5,584,070 A | 12/1996 | Harris et al. | |
| 5,598,201 A | 1/1997 | Stodder et al. | |
| 5,600,350 A | 2/1997 | Cobbs et al. | |
| 5,600,352 A | 2/1997 | Knierim et al. | |
| 5,606,347 A | 2/1997 | Simpson | |
| 5,610,635 A | 3/1997 | Murray et al. | |
| 5,620,265 A | 4/1997 | Kondo | |
| 5,625,391 A | 4/1997 | Hirabayashi et al. | |
| 5,629,981 A * | 5/1997 | Nerlikar | 713/168 |
| 5,644,557 A | 7/1997 | Akamine et al. | |
| 5,647,679 A | 7/1997 | Green et al. | |
| 5,661,515 A | 8/1997 | Hevenor et al. | |
| 5,700,623 A | 12/1997 | Anderson et al. | |
| 5,713,288 A | 2/1998 | Frazzitta | |
| 5,721,992 A | 2/1998 | Chovanes | |
| 5,755,519 A | 5/1998 | Klinefelter | |
| 5,757,021 A | 5/1998 | Dewaele | |
| 5,757,394 A | 5/1998 | Gibson et al. | |
| 5,768,633 A | 6/1998 | Allen et al. | |
| 5,774,639 A | 6/1998 | Schildkraut et al. | |
| 5,774,752 A | 6/1998 | Patton et al. | |
| 5,790,216 A | 8/1998 | Inbar et al. | |
| 5,812,156 A | 9/1998 | Bullock et al. | |
| 5,828,774 A * | 10/1998 | Wang | 382/128 |
| 5,842,118 A | 11/1998 | Wood, Jr. | |
| 5,850,481 A | 12/1998 | Rhoads | |
| 5,875,249 A | 2/1999 | Mintzer et al. | |
| 5,912,972 A | 6/1999 | Barton | |
| 5,913,088 A | 6/1999 | Moghadam et al. | |
| 5,914,671 A | 6/1999 | Tuttle | |
| 5,949,885 A | 9/1999 | Leighton | |
| 6,031,516 A | 2/2000 | Leiper | |
| 6,031,914 A | 2/2000 | Tewfik et al. | |
| 6,041,335 A * | 3/2000 | Merritt et al. | 715/512 |
| 6,044,156 A | 3/2000 | Honsinger et al. | |
| 6,075,950 A | 6/2000 | Stephenson | |
| 6,096,491 A | 8/2000 | Majumdar et al. | |
| 6,099,178 A | 8/2000 | Spurr et al. | |
| 6,106,166 A | 8/2000 | Spurr et al. | |
| 6,124,083 A | 9/2000 | Majumdar et al. | |
| 6,157,373 A | 12/2000 | Rego | |
| 6,173,119 B1 | 1/2001 | Manico et al. | |
| 6,227,643 B1 | 5/2001 | Purcell et al. | |
| 6,263,310 B1 | 7/2001 | Loudermilk et al. | |
| 6,275,825 B1 * | 8/2001 | Kobayashi et al. | 707/9 |
| 6,282,819 B1 | 9/2001 | Gu | |
| 6,327,972 B1 * | 12/2001 | Heredia et al. | 101/35 |
| 6,353,672 B1 | 3/2002 | Rhoads | |
| 6,381,418 B1 * | 4/2002 | Spurr et al. | 396/310 |
| 6,577,238 B1 * | 6/2003 | Whitesmith et al. | 340/572.1 |
| 6,608,551 B1 * | 8/2003 | Anderson et al. | 340/10.51 |
| 6,823,459 B1 * | 11/2004 | Horikoshi et al. | 726/17 |
| 6,920,330 B1 * | 7/2005 | Caronni et al. | 455/456.1 |
| 2002/0010679 A1 * | 1/2002 | Felsher | 705/51 |
| 2002/0076091 A1 * | 6/2002 | Wang | 382/132 |
| 2002/0101619 A1 | 8/2002 | Tsubaki et al. | |
| 2002/0184159 A1 * | 12/2002 | Tadayon et al. | 705/54 |

| | | | | |
|---|---|---|---|---|
| 2003/0128099 | A1* | 7/2003 | Cockerham | 340/5.7 |
| 2003/0172034 | A1* | 9/2003 | Schneck et al. | 705/54 |
| 2004/0049733 | A1* | 3/2004 | Kerr et al. | 715/512 |
| 2004/0153671 | A1* | 8/2004 | Schuyler et al. | 713/201 |
| 2004/0246270 | A1* | 12/2004 | Krishnamurthy et al. | 345/634 |

FOREIGN PATENT DOCUMENTS

| | | |
|---|---|---|
| JP | 06-044265 | 7/1992 |
| NL | 9400392 | 3/1994 |
| WO | WO 98/52762 | 11/1998 |

OTHER PUBLICATIONS

TEMIC Semiconductors, e5550—Standard Read/Write Identification IC, Rev. A3, Mar. 17, 1998, pp. 1-11.

HID Corp., Multi-Technology Card Guide, pp. 1, www.hidcorp.com/products.

HID Corp., ProxCard®II, Proximity Access Card, pp. 1-2, www.hidcorp.com/products.

HID Corp., ISO Thin Card, pp. 1-2, www.hidcorp.com/products.

Protective Security Management, HID Prox Cards, pp. 1, www.prosecman.com.au.

Atmel Corp., Atmel Smart Card ICs, 2000, pp. 1-12.

Texas Instruments, Tag-it™—Moving Concepts to Reality, pp. 1-13, 2000.

Texas Instruments, Making RFID work for you: An Industry Roundtable hosted by Texas Instruments at NACS-Tech 1998, 2000, pp. 1-15, www.ti.com/tiris.

Texas Instruments, d'Hont, The Cutting Edge of RFID Technology and Applications for Manufacturing and Distribution, pp. 1-13, www.ti.com/tiris.

Atmel Corp., Atmel Read-Only Transponder—TK5530, Rev. A5, Dec. 19, 2001, pp. 1-10, www.atmel-wm.com Philips Semiconductors, mifare Standard Card IC MFI IC S50 Functional Specification, Rev. 5.1, May 2001, pp. 1-19, www.semiconductors.philips.com.

Texas Instruments, Radio Frequency Identification Systems—Access Control, pp. 1-2, www.ti.com/tiris/docs/solutions/solutions.shtml.

Texas Instruments, Michael Knebelkamp, et al., Latest Generation Technology for Immobilizer Systems, www.ti.com/tiris.

* cited by examiner

ILLUMINATION APPARATUS

CROSS REFERENCE TO RELATED APPLICATIONS

Reference is made to commonly assigned co pending patent application Ser. No. 10/161,514 entitled VIRTUAL ANNOTATION OF A RECORDING ON AN ARCHIVAL MEDIA filed in the name of Kerr et al. on Jun. 3, 2003.

FIELD OF THE INVENTION

The invention generally relates to an illumination device for viewing image transparences and more particularly an illumination device for viewing image transparences and information related thereto.

BACKGROUND OF THE INVENTION

Information systems such as Hospital Information Systems (HIS) or Radiology Information Systems (RIS) provide information management for medical data for patients admitted to hospitals or receiving outpatient care. Patient information can be in multitude of forms serving functions such as patient records, billing and medical diagnostic films. Diagnostic films are generated by several modalities such as Computer Tomography, Ultra Sound, Magnetic Resonance Imaging, Digital Radiographic or Computer Radiographic using a many different devices that generate images with a wide variety of mediums using different exposure, processing and development techniques. Accordingly, diagnostic images are generated with a wide variety of image densities, color qualities and media properties that are best observed under lighting conditions that reflect such characteristics and properties.

Many types of diagnostic images are formed digitally and printed onto diagnostic film with the digital data typically retained, allowing reprinting of the diagnostic film at a later time, thus reducing dependence on a single piece of diagnostic film that could be misplaced or inadvertently destroyed. However, other types of patient related records and diagnostic images are routinely recorded only on hardcopy diagnostic films and paper files held in folders. Such folders continue to serve as the ultimate repository of medical information for each patient. It is vital for effective patient care that such films contain not only the correct diagnostic films and records needed to diagnose and treat a patient's condition but also that the diagnostic films and records are positively identified so that there is minimal chance of confusion due to mismatched diagnostic films. It is also valuable to ensure that such diagnostic films be correlated with other data about the patient. Finally, it is also important that patient privacy be properly maintained, with checks on authorization and security that help to ensure the privacy of patient records and help to obtain the proper medical care, without jeopardizing quality and timeliness. These needs are not met by the current folder based system. Thus, there remains a recognized need for more efficient ways of maintaining and managing hardcopy diagnostic films and for associating these diagnostic films to the complete set of patient data.

An important tool in observing diagnostic films is the conventional illumination device also called a light box. This device has a display platform that projects a generally uniform light pattern in a manner that passes through diagnostic films in order to facilitate observation of these diagnostic films. Diagnostic images, printed on film, show the appropriate detail with the sufficient backlight illumination. However, the conventional illumination device provides only one kind of light for viewing such diagnostic films. The light does not adapt to the characteristics of the diagnostic film being viewed using the illumination device.

Further, there can be a need to view both diagnostic films in concert with digital images of and or textual data patient data. Solutions have been proposed for a hybrid illumination device for conventional diagnostic films and for digital images and or textual data patient data. For example, U.S. Pat. No. 6,031,516 entitled "Integrated Film and Film less Image Display System" to Leiper discloses a viewing workstation that allows a medical professional to access and view an X-ray image from a roll of images. Then, from a bar code on the X-ray, a link is provided to electronically stored images for the same patient. These images are then displayed on a display monitor.

Related solutions include U.S. Pat. No. 5,790,216 entitled "Viewing Apparatus and Work Station" to Inbar et al., which also discloses a backlight apparatus having an auxiliary display for electronic data. U.S. Pat. No. 6,157,373 entitled "Method and Apparatus for Displaying Images" to Rego discloses sensing a bar code or other indicia on a film image for obtaining an electronic image, including use of a touch-sensitive display surface for displayed films.

While the solutions of Leiper '516, Inbar et al. '216, and Rego '373 disclosures provide the capability for viewing both film and electronic data and images, there is substantial room for improvement with respect to image management, access security and log maintenance, and user interaction. For example, For example, there are numerous additional opportunities for improvement of diagnosis and treatment using a digital light box as part of a larger medical imaging system.

The Leiper '516 and Rego '373 disclosures describe sensing a bar code for obtaining the electronic image data that corresponds to an image on film. The bar code thus provides a read-only "pointer" to the larger database. A number of other types of memory devices can be coupled to a specific piece of image-bearing film. Examples of suitable memory devices include other optically encoded devices and magnetic strips or similar magnetically encoded media.

Radio frequency identification devices offer yet another type of solution for associating a memory storage device with a unit of an imaging medium. Radio frequency identification tags have been proposed for use in a wide range of identification and tracking applications, such as with passports and credit cards, as is disclosed in U.S. Pat. No. 5,528,222 to Moskowitz et al. One type of commercially available, low profile radio frequency identification tags is the "TAG-IT INLAY"™ RFID tag available from Texas Instruments, Incorporated, located in Dallas, Tex., USA. This component can be used to provide identifying information about an item to which it is attached, for example. radio frequency identification devices are useful for tracking the location of, characteristics of and usage of documents, books, packages, and other inventory. For example, radio frequency identification tags can be used to track the location of documents and track the chain of custody of such documents within a document management system. Radio frequency identification tags offer the advantage of small size, enabling these devices to be unobtrusively attached or embedded within an item. Unlike optical or mechanical equivalents, radio frequency identification tags allow communication regardless of orientation relative to a transceiver. When equipped with an on-board read-write memory, these devices can be used for recording and recall of at least some amount of data related to an item to which they are coupled.

Systems employing radio frequency identification tags typically comprise a read/write element, or radio frequency transceiver, that acts as the interface between the radio frequency identification tags and a computer system of some type that uses and/or provides the stored data. The radio frequency identification tags itself is typically embodied as a transponder, having an integral antenna, adapted to send and receive electromagnetic fields in cooperation with the transceiver, where the electromagnetic field itself contains information to be conveyed to and from a memory on the radio frequency identification tags. Both read/write and read-only versions of radio frequency identification tags are available. Information that is stored in memory on the radio frequency identification tags can be used to track, identify, and process an item. The radio frequency identification tags memory can also store other information that is to be associated with the item, such as timestamps and identification codes for example. Among possible uses for radio frequency identification tags are identification, tracking, and management of diagnostic films such as X-ray films. However, some type of data processing and display platform is needed in order to associate a diagnostic film with the full body of medical information available for a patient and to provide secure access to that data.

Thus, it can be seen that there is a need for an illumination device that enables viewing of diagnostic films with access to related electronic diagnostic images and available patient data to an attending diagnostician having the proper authorizations.

SUMMARY OF THE INVENTION

In one aspect of the invention, a viewing device is provided for viewing at least one image transparency having an associated tracking memory. The viewing device comprises an illumination device having at least one viewing surface adapted to present at least one illumination pattern, at least one radio frequency read write device for obtaining electronic data stored in an associated tracking memory of an image transparency positioned proximate to the viewing surface and at least one display device for viewing at least one electronic image related to said at least one image transparency. A control processing unit is adapted to receive said obtained data from said associated tracking memory and to use the obtained data for forming the at least one electronic image.

In another aspect of the invention, a viewing device is provided for viewing at least one image transparency having an associated tracking memory. The viewing device has an illumination device having at least one viewing surface adapted to present at least one illumination pattern, at least one radio frequency read write device for obtaining electronic data stored in an associated tracking memory of an image transparency positioned proximate to the viewing surface; and a display device adapted to form at least one electronic image related to said at least one image transparency. A control processing unit is adapted to receive said obtained data from said associated tracking memory and to use the obtained data for forming the at least one electronic image and for controlling the appearance of at least one illumination pattern.

In still another embodiment of the invention, a viewing device is provided for viewing an image transparency having a tracking memory. The apparatus has a means for reading data from the tracking memory, a means for presenting at least one image on a display surface and a means for forming an illumination pattern for viewing an image transparency. A means is provided for using the obtained data in presenting at least one of the electronic image and the illumination pattern.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Figure 1:
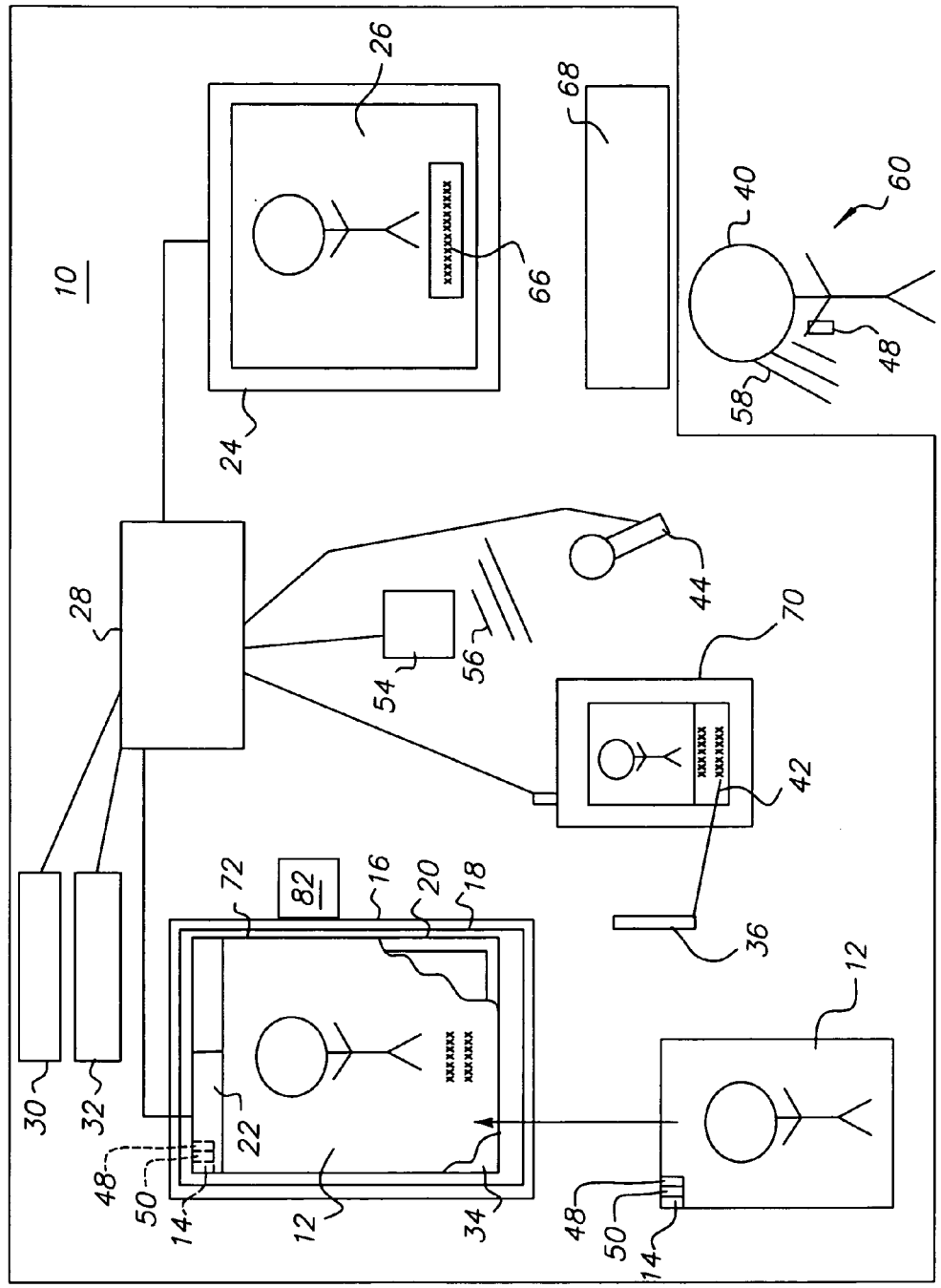
FIG. 1. is a schematic block diagram showing one embodiment of a viewing device and related components of the present invention.

Referring to FIG. 1, there is shown a viewing device 10 with an arrangement of related components for viewing by a viewer 40 at least one image transparency 12 having an associated tracking memory 14 that can be in the form of a radio frequency transponder 48. Radio frequency transponder 48 can be a passive or active type transponder. Radio frequency transponder 48 can have a rewritable memory or a static memory. Viewing device 10 has an illumination device 16 having at least one viewing surface 18 adapted to present at least one illumination pattern 20, a radio frequency read write circuit 22 for obtaining and exchanging electronic data stored in the associated tracking memory 14 of the at least one image transparency 12 positioned proximate to the at least one viewing surface 18. A control-processing unit 28 is provided and adapted to receive the obtained data from the associated tracking memory 14. Control processing unit 28 can comprise a programmable micro-processor, micro-controller or other control circuit. Control processing unit 28 controls at least one display device 24 and causes display device 24 to present at least one at least one electronic image or related data 26 related to the at least one image transparency 12.

Control processing unit 28 can also be adapted to cause display device 24 to present menu selections and other features for exchanging information and instructions between viewer 40 and control processing unit 28. Such information and instructions can be exchanged using for example, the a text window 66 shown in FIG. 1 and a user interface 68 such as a keyboard, console, voice recognition system or other input system for entry or review of text data.

Control processing unit 28 is further adapted to use the obtained data from the associated tracking memory for forming the at least one electronic image. In one aspect this can be done by obtaining a patient related image or patient related data from a database 30, a network database 32 or from the tracking memory 14 associated with said image transparency 12, or from a piece of medical monitoring equipment (not shown) that monitors the condition of a patient. Control processing unit 28 further causes at least one electronic image or related data 26 to be presented by the at least one display device 24.

Control processing unit 28 causes at least one illumination pattern 20 to be generated by illumination device 16. Light from illumination pattern 20 passes through at least one image transparency 12 and the appearance of the at least one illumination pattern 20 can be determined based upon data obtained from a database 30, a network database 32 or from the tracking memory 14 associated with said image transparency 12.

In this regard, the data obtained from tracking memory 14 is used to make adjustments to illumination pattern 20 to ensure that each image transparency 12 is illuminated in a fashion that best suits the characteristics of image transparency 12. It will be appreciated that each image transparency associated with a patient is captured at a different time and the that it is often the case that they are captured using different equipment. Sometimes different media is used to capture the image. Accordingly, image densities and other characteristics of image transparency 12 such as a density adjustment curve for image transparency 12, can be obtained using the data obtained from tracking memory 14. Such data can include but is not limited to data that identifies the media type, date of image formation, equipment used for image formation, and information characterizing the imaging process used to form the image. Control processing unit 28 uses this information to form illumination area 18 having an appearance that will optimize the appearance of image transparency 12 when light from the illumination area 18 is viewed through image transparency 12. This can help a medical professional to compare image transparencies that are captured at different times in different ways and using different techniques and media.

In one embodiment, the viewing surface 18 of the illumination device 16 can be a touch screen 34. Touch screen 34 can be adapted to automatically size the illumination pattern 20 to the outline of the image transparency 12. Control processing unit 28 receives a signal from touch screen 34 and causes illumination device 16 to generate an illumination pattern 20 that is arranged so that light from illumination pattern 20 passes light through the image transparency 12. Touch screen 34 can also be used as an input device to receive instructions and information from a viewer 40. In other embodiments a sensors such as light sensors, capacitance sensors and other positional sensors (not shown) can sense the position of image transparency 12 and can provide information locating image transparency on illumination device 16 from which control processing unit 28 can generate an illumination pattern for viewing image transparency 12. Viewing device 10 also provides a viewing area radio frequency read write device 54 for obtaining information from a radio frequency transponder 48 that is associated with a viewer 40 within a viewing area 60. Viewing area radio frequency read write device 54 can comprise any form of transducer or other device capable of sending a first electromagnetic field 56, receiving a second electromagnetic field 58 from radio frequency transponder 48 in response to the first electromagnetic field 56. Viewing area radio frequency read/write device 54 converts the received second electromagnetic field 58 into a form that can be used by control processing unit 28 in operating viewing device 10. If no second electromagnetic field 58 is received in response to the first electromagnetic field 56 no illumination pattern 20 is illuminated. If an appropriate second electromagnetic field 58 is received in response to the first electromagnetic field 56 an illumination pattern 20 is illuminated. Information regarding the viewer 40 can be recorded such as in the memory 50 of the associated tracking memory 14, data base 30, network data base 32, or the radio frequency transponder 48 associated with the viewer 40.

Viewing device 10 device can also be controllable in regards to viewing security using preset access permissions (not shown) stored in the memory 50 of the associated tracking memory 14, data base 30, network data base 32, and radio frequency transponder 48 associated with the viewer 40 that can control illumination of the illumination device 16 or limit access to electronic images or related data 26 that can be shown on the display device 24. For example, the information obtained from tracking memory 14 can be used to define access privileges required for viewing patient related data. Information stored in radio frequency transponder 48 can then be used to determine viewing privileges for viewer 40. Where the access privileges obtained using data from the tracking memory correspond with viewing privileges determined for viewer 40, control processing unit 28 can permit illumination device 16 to generate an illumination pattern for viewing an image transparency. Conversely where the access privileges obtained using data from the tracking memory do not correspond with viewing privileges determined for viewer 40, control processing unit 28 can prohibit illumination device 16 from generating an illumination pattern for viewing an image transparency and from providing any other form of patient related data. In this way, viewing device 10 cannot be used by viewer 40 to observe an image transparency 12, other patient related images and patient related content unless viewer 40 is authorized to view such content.

An optional audio input system 44 can be provided that allows the capture and storage of audio data or transcription to text, including transcription performed off-site. An optional tablet computing device 70 can be provided with a stylus 36 for handwritten data entry in a text entry surface 42. As noted above, the viewing surface 18 of illumination device 16 can also optionally be provided touch screen 34 for accepting handwritten input using stylus 36 or some other writing device. Thus, physicians or other medical professionals can provide annotations that will be associated with image transparency 12 directly and can have this annotation stored electronically as part of the patient's medical record either by storage in database 30 or by storage in tracking memory 14. Other forms of input systems can be used for such purposes including but not limited to systems such as a touch pad input, a 4-way switch, a 6-way switch, an 8-way switch trackball system, a joystick system, a keypad system, a mouse system, a gesture recognition system or other such systems.

When image transparency 12 is placed onto viewing surface 18 having a touch screen 34, radio frequency read/write circuit 22 detects the image transparency 12 and causes viewing surface 18 to illuminate a masked area 72, corresponding to the outline of image transparency 12. Image transparency 12 is then illuminated to provide illumination only to image transparency 12. This has the advantageous effect of minimizing or eliminating glare from portions of illumination pattern 20 that do not pass through image transparency 12. A similar masking utility for a backlighting display is disclosed in U.S. Pat. No. 6,279,253 entitled "Self-Masking Transparency Viewing Apparatus" to Inbar et al.

The dimensions and location of masked area 72 are sensed from information encoded on associated tracking memory 14, as described subsequently. Alternately, viewing surface 18 having a touch screen 34 may sense the size and position of image transparency 12 using for example, a positional sensor (not shown) such as light sensors, capacitance sensors, touch screen type sensors and conventional contact electro-mechanical switches, with positional sensor (not shown) providing a signal that indicates an area of the viewing surface 18 that corresponds to the position of image transparency 12. This causes illumination device 16 to illuminate a masked area 72 that confronts the image transparency 12. Brightness controls 82 are provided. Optionally, color tint of masked area 72 can be adjusted using similar on-screen interface color tint tools (not shown), such as a sliding bar icon.

Patient privacy is one area of concern for allowing access to diagnostic images. Policies at a medical facility and/or legal requirements may dictate that only designated medical providers have access to particular medical image transparencies 12 and other patient information. In addition, there may be various levels of restriction enforced. For example, one set off medical providers for a patient may have unlimited access to the complete medical record, including all images and patient data. However, another set of medical providers may be permitted access only to specific images and data relevant to a particular injury or treatment.

Figure 2:
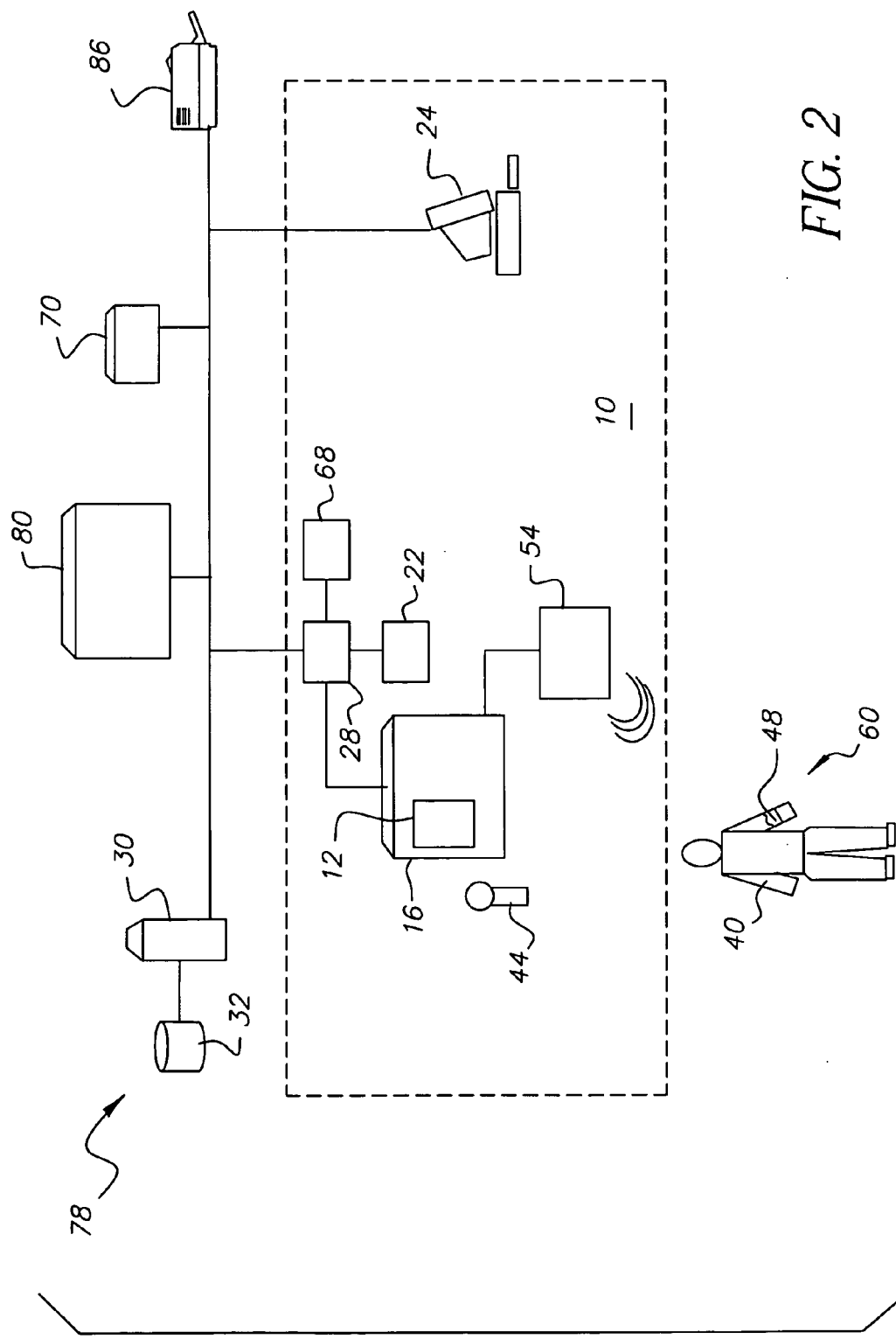
FIG. 2. is a schematic block diagram illustrating the use of on embodiment of a viewing device of the present invention as part of a larger networked medical diagnostic imaging system.

Referring to FIG. 2, viewing device 10 is shown as part of a larger records maintenance system 78. In the embodiment of FIG. 2, records maintenance system 78 includes a patient database 30, which contains one or both of patient data and medical images, one or more image capture systems 80, such as X-ray or ultrasound apparatus.

A viewer 40 can access data from viewing device 10 in a number of ways. In conventional networked systems, a login and password, entered on a keyboard, are required for access to image display. In the embodiment of FIG. 2, a radio frequency transponder 48 associated with viewer 40 automates access security routines and, identifies viewer 40 as having specific access permissions, minimizes or eliminates the need for login and password entry. Additional authentication processes may be required and executed using user interface 68. Detection of viewer 40 is similar to detection of the associated tracking memory 14 that is associated with image transparency 12.

Once control processing unit 28 validates the identity and access permissions of viewer 40 and obtains data from the associated tracking memory, access is provided to various other subsystems of diagnostic imaging and records maintenance system 78. Information can be accessed from a database 30, including electronic images, patient history, billing data, and related information. An image capture system 80 may also be accessed, allowing updated images transparencies 12 to be downloaded directly to viewing device 10. Image capture system 80 may be, for example, an X-ray or ultrasound imaging system.

As shown in FIG. 2, viewing device 10 serves as an access point for obtaining and updating data and image information across the complete diagnostic imaging and records maintenance system 78. An optional printer 86 enables viewer 40 to obtain a copy of one or more specific images or data for a patient.

As shown in the above description, viewing device 10 of FIG. 1 provides a platform for interaction with the overall diagnostic imaging and records maintenance system 78 of FIG. 2. There are a number of options for initiating and validating the use of viewing device 10. In the mode of access described hereinabove, viewer 40 positions image transparency 12 against viewing device 10 to initiate viewing operation. Radio frequency read write device 22, obtains the necessary information from the associated tracking memory 14 to identify the image transparency 12. Viewing area radio frequency read write device 54, obtains the necessary information from radio frequency transponder 48 associated with the viewer 40. Control processing unit 28 then validates and, optionally authenticates, viewer 40 permissions, in conjunction with database 30. Viewer 40, once authorized, is then permitted access to some or all of the patient images and data from patient database 30.

One benefit of viewing device 10 as part of diagnostic imaging and records maintenance system 78 relates to the automated identification of viewer 40, whether or not manual login and password entry are used. This capability facilitates the maintenance of an electronic log that records information such as: what images were viewed at a particular time, and identity of viewer 40, the medical professional who accessed and viewed the images and patient data. The stored information also provides tracking data, including information on which medical professional has possession of a patient image or folder, for example.

Another benefit of the viewing device 10 of the present invention relates to facility of annotation. Viewing device 10 provides a useful mechanism for recording various notes, instructions, and observations from members of the diagnosis and treatment staff Annotation can be obtained in a number of different ways. Comments and annotation can be obtained while a medical professional is observing an image transparency 12. Such comments and annotations can be obtained and converted into digital form using text based, video based, graphics based and or audio based embodiments. The digital data can be stored in a database 30 or in some storage facility linked to database 30. Alternately, audio comments could be transcribed. Using a transcription service, viewer 40 can simply make observations into audio capture system 44 and have text automatically stored in a file in database 30 and/or displayed on display device 24 in text window 66. Transcription services could even be remotely located, using either human operators or speech recognition and text conversion software, for example. Viewer 40 could then display transcribed text in for example, text window 66 of FIG. 1, enabling editing and correction.

Similarly, written annotation can be obtained and recorded in a number of ways. As FIG. 1 above shows, tablet 70 and stylus 36 provide one mechanism for annotation capture. Optionally, viewing surface 18 could be a touch screen 34 for accepting written annotation. This would enable recording of any handwritten text written on any part of viewing surface 18, including masked area 72.

The ability to write data to associated tracking memory 14 is another advantage of the present invention when using radio frequency components. Unlike the barcode encoding described in the '516 Leiper disclosure, the radio frequency transponder 48 encoding can be modified. Thus, viewing device 10 can update the radio frequency transponder 48, including the capability to store alternate or updated images on the radio frequency transponder 48.

Other advantages of the use of tracking memory 14 comprising an RFID component include proximity scanning, so that it is not necessary for viewer 40 to separately "swipe" the radio frequency transponder 48 past a sensor, as is required with bar encoding and magnetic strips.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

PARTS LIST 10 viewing device
12 image transparency
14 associated tracking memory
16 illumination device
18 viewing surface
20 illumination pattern
22 radio frequency read write device
24 display device
26 electronic image or related data
28 control processing unit
30 database
32 network database
34 touch screen
36 stylus
40 viewer
42 text entry surface
44 audio input system
46 network address
48 radio frequency transponder
50 memory
52 patient identification information
54 viewing area radio frequency read write device
56 first electromagnetic field
58 second electromagnetic field
60 viewing area
64 wireless antenna
66 text window
68 user interface
70 tablet PC
72 masked area
76 optional text area
78 records maintenance system
80 image capture system
82 brightness controls
86 optional printer

What is claimed is:

1. A viewing device for viewing at least one image transparency having an associated tracking memory, the viewing device comprising:
    an illumination device having at least one viewing surface adapted to present at least one illumination pattern;
    at least one radio frequency read write device for obtaining electronic data stored in the tracking memory of an image transparency positioned proximate to the viewing surface said tracking memory having a set of access privileges stored therein;
    at least one display device for viewing at least one electronic image related to said at least one image transparency; and
    a viewing area radio frequency read write device adapted to send a first electromagnetic field into a viewing area and to receive a second electromagnetic field sent from at least one radio frequency transponder associated with at least one viewer in response to the first electromagnetic field, said second electromagnetic field having information stored in a memory of the at least one radio frequency transponder, said stored information including information from which viewing privileges can be determined; and
    a control processing unit adapted to receive said obtained data from said associated tracking memory and to use the obtained data for forming the at least one electronic image, said control processing unit being adapted to use information obtained from the tracking memory to define access privileges required for viewing patient related data, without reference to external data sources, and to determine viewing privileges for any identified viewer from information provided in any received second electromagnetic field, said control processing unit being adapted to prevent the illumination device and the display device from facilitating viewing of an image transparency, other patient related images, or patient related content unless the defined access privileges correspond to the determined viewing privileges.

2. The viewing device of claim 1, wherein the control processing unit uses the obtained data from said associated tracking memory to obtain a patient related image from a database and forms the at least one electronic image based upon the obtained patient related image.

3. The viewing device of claim 1, wherein the control processing unit uses the obtained data from said associated tracking memory to obtain patient related data and forms the at least one electronic image based upon the obtained patient related data.

4. The viewing device of claim 1, wherein the control processing unit forms the at least one electronic image using at least one of a patient related image and patient related data that is stored in the tracking memory.

5. The viewing device of claim 4, wherein the at least one of the patient related image and patient related data is stored in a network database.

6. The viewing device of claim 1, wherein once the control processing unit validates the identity and access permissions of viewer and obtains data from the associated tracking memory, the control processing unit is provided access to data stored in a diagnostic imaging system or a records maintenance system.

7. The viewing device of claim 1, wherein at least one illumination pattern is generated by the illumination device for passing through at least one image transparency and wherein the appearance of said at least one illumination pattern is determined based upon data obtained from said associated tracking memory associated with said at least one image transparency.

8. The viewing device of claim 1, wherein the at least one illumination pattern is determined based upon data obtained from said associated tracking memory associated with said at least one image transparency.

9. The viewing device of claim 1, wherein said at least one viewing surface comprises a touch screen.

10. The viewing device of claim 9, further comprising a stylus for performing annotations on said viewing surface.

11. The viewing device of claim 1, wherein at one of the at least illumination patterns comprises a generally uniform illumination area and the control processing unit automatically shapes the generally uniform illumination area to correspond with an outline of the image transparency and arranges the generally uniform illumination area so that light from the illumination area passes through the image transparency.

12. The viewing device of claim 1, wherein one of said at least one illumination pattern comprises a generally uniform illumination area wherein the viewing device comprises a sensor for detecting a viewer action that defines the size and placement of the illumination area.

13. The viewing device of claim 1, wherein said radio frequency read write device comprises a radio frequency transponder.

14. The viewing device of claim 1, further comprising a text entry system for receiving an annotation.

15. The viewing device of claim 1, further comprising an audio input system for recording audio information about the at least one image transparency.

16. The viewing device of claim 1, wherein the associated tracking memory stores a network address for the at least one electronic image or related data.

17. The viewing device of claim 1, wherein the associated tracking memory is a radio frequency transponder.

18. The viewing device of claim 17, wherein the radio frequency transponder has a memory for storing the patient identification information.

19. The viewing device of claim 1, wherein the tracking memory also stores information about characteristics of the image transparency and the control-processing unit adjusts the appearance of the image based upon said illumination characteristics stored in memory.

20. The viewing device of claim 1, wherein if no second electromagnetic field is received in response to the first electromagnetic field no illumination pattern is illuminated.

21. The viewing device of claim 20, wherein if a second electromagnetic field is received in response to the first electromagnetic field an illumination pattern is illuminated.

22. A viewing device having for viewing at least one image transparency having an associated tracking memory, comprising:
   an illumination device having at least one viewing surface adapted to present at least one illumination pattern;
   a display device adapted to form at least one electronic image related to said at least one image transparency;
   a radio frequency read write device for obtaining electronic data stored in a tracking memory of an image transparency positioned proximate to the viewing surface, said electronic data including access privilege information and for obtaining electronic data including viewing privilege information stored in a radio frequency transponder associated with at least one viewer in a viewing area; and
   a control processing unit adapted to receive said obtained data from said associated tracking memory and to use the obtained data for forming the at least one electronic image and for controlling the appearance of at least one illumination pattern;
   wherein the control processing unit does not allow the illumination device to form an illumination area for viewing the image transparency or to present the formed image unless the control processing unit determines that the access privilege information corresponds to the viewing privilege information.

23. The viewing device of claim 22, wherein the at least one electronic image comprises an image that depicts subject matter that is similar to the subject matter of the image transparency but captured at a different time.

24. The viewing device of claim 22, wherein the at least one electronic image comprises an annotation for the image transparency image.

25. The viewing device of claim 22, wherein the illumination area and the electronic image at least partially overlap.

26. A viewing device for viewing an image transparency having a tracking memory; the apparatus comprising:
   a means for reading data from the tracking memory and means for obtaining data from a radio frequency transponder associated with at least one viewer in a viewing area, said data including viewing privilege data;
   a means for presenting at least one image on a display surface;
   a means for forming an illumination pattern for viewing the image transparency so that the transparency can be viewed in the viewing area;
   a means for using the obtained data in presenting at least one of the electronic image and the illumination pattern; and,
   a means for operating the illumination device so that the illumination device does not form an illumination area for viewing the image transparency unless the control processing unit determines, from the data obtained from the tracking memory and from the data obtained from the radio frequency transponder associated with the viewer that the viewer is authorized to view the image transparency.

27. The viewing device of claim 26, wherein the means for using the obtained data in presenting at least one of the electronic image and the illumination pattern is adapted to use the obtained data to access data comprising at least one of a patient related image and patient related data and to use the accessed data to form the electronic image.

28. The viewing device of claim 26, wherein the means for using the obtained data in presenting at least one of the electronic image and the illumination pattern is adapted to use the obtained data to access data indicating at least one of information about the image transparency, the time that the image was recorded on the image transparency and the imaging process used to record the image on the image transparency and to use the accessed data to form the electronic image.

29. The viewing device of claim 26, further comprising means for detecting viewers proximate to the viewing device, to use the obtained data to determine whether the detected viewers are authorized to view the image transparency and means for preventing the formation of an illumination area where at least one viewer is not authorized to view the image transparency.

* * * * *